United States Patent
Takahashi et al.

(10) Patent No.: US 6,455,745 B1
(45) Date of Patent: Sep. 24, 2002

(54) MANUFACTURING METHOD FOR FLUORINE-CONTAINING ETHANE

(75) Inventors: Kazuhiro Takahashi; Satoru Kono; Takashi Shibanuma, all of Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/743,468

(22) PCT Filed: Jul. 16, 1999

(86) PCT No.: PCT/JP99/03868

§ 371 (c)(1), (2), (4) Date: Jan. 10, 2001

(87) PCT Pub. No.: WO00/03962

PCT Pub. Date: Jan. 27, 2000

(30) Foreign Application Priority Data

Jul. 17, 1998 (JP) .......................................... 10-203515

(51) Int. Cl.$^7$ ............................................... C07C 17/08
(52) U.S. Cl. ....................................... 570/166; 570/168
(58) Field of Search ................................... 570/166, 168

(56) References Cited

U.S. PATENT DOCUMENTS 4,158,675 A * 6/1979 Potter .......................... 570/166
5,334,787 A  8/1994 Felix et al.
5,399,549 A  3/1995 Felix et al.

FOREIGN PATENT DOCUMENTS

| JP | 5-146680  | 6/1993 |
| JP | 8-38904   | 2/1996 |
| JP | 9-141105  | 6/1997 |
| JP | 10-500595 | 1/1998 |

* cited by examiner

*Primary Examiner*—Alan Siegel
(74) *Attorney, Agent, or Firm*—Armstrong, Westerman & Hattori, LLP

(57) ABSTRACT

Fluorochromium oxide having a fluorine content of not less than 30 wt. % is used for the fluorination reaction.

To provide a manufacturing method for fluorine-containing ethane which contains 1,1,1,2,2-pentafluoroethane as the main component in which the reaction can be performed while controlling the generation of CFCs to the greatest possible extent by fluorinating at least on selected from the group composed of tetrachloroethylene, 2,2-dichloro-1,1,1-trifluoroethane and 2-chloro-1,1,1,2-tetrafluoroethane with hydrogen fluoride.

6 Claims, No Drawings

MANUFACTURING METHOD FOR FLUORINE-CONTAINING ETHANE

This application is a 371 of PCT/JP99/03868 filed Jun. 16, 1999.

FIELD OF THE INVENTION

The present invention relates to a manufacturing method for fluorine-containing ethane to obtain 2-chloro-1,1,1,2-tetrafluoroethane (in places abbreviated to HCFC-124) and/or 2,2-dichloro-1,1,1-trifluoroethane (in places abbreviated to HCFC-123) as well as 1,1,1,2,2-pentafluoroethane (in places abbreviated to HFC-125) as the main reaction products.

PRIOR ART

HFC 125 is used as a component in an alternative refrigerant gas to 1-chloro-1,1-difluoromethane (HCFC-22), because its ozone destruction coefficient is 0. Among manufacturing methods for HFC-125 using HCFC-124 as the material, a manufacturing method using chromium oxide ($Cr_2O_3$) as the catalyst is described in publication U.S. Pat. No. 5,475,167 as a paten for controlling the generation of CFCs (which are currency banned because they cause damage to the ozone layer). In the method described in this publication, a conversion to HCFC-125 of not less than 50% is said to be necessary. Also, in the method described in the Examples, a $Cr_2O_3$ catalyst with high specific surface area prepared from $(N_4)_2Cr_2O_7$ or one which is further treated with CO, $H_2$ and $H_2O$ is used. When using these catalysts, the amount of CFCs generated is 0.3 mol % of the HFC-125.

Further, in publication U.S. Pat. No. 5,334,787, a manufacturing method for HFC-125 through a gas phase reaction from HCF-123 or HCFC-124 is described which uses $Cr_2O_3$ as the catalyst. According to this description, an increase in the generation rate is necessary in order to control the generation ratio of CFCs to less than 2%. However, there is no detailed description of the actual generation ratio. Similarly in publication U.S. Pat. No. 5,399,549, a manufacturing method for HFC-125 through a gas phase reaction from the same starting material is described which uses $Cr_2O_3$ as the catalyst. However, there is no detailed description of the generation ratio of CFCs.

On the other hand, in Japanese Patent Laid-Open No. 247,883/94 a manufacturing method for HFC-125 characterized by a controlled low amount of CFCs generated is disclosed which uses a catalyst of alumina fluorinated to over 70% in a fluorination reaction of HCFC-123 or HCFC-124. According to this manufacturing method, although the amount of CFCs generated in the fluorination reaction of HCFC-123 with the alumina catalyst is 0.5% at a reaction temperature of 350° C., the ratio of CFCs/HFC-125 is high at about 1.1%.

A fluorination method for tetrachloroethylene with a catalyst of fluorinated alumina is described in Japanese Patent Laid-Open No. 505,328/91 in which a method is disclosed that use a catalyst of alumina containing over 90 wt. % of $AlF_3$ and carrying metals such as Cr and Mn. This publication, however, includes no description of impurities such as CFCs.

With regard to other methods, although similar methods are also disclosed in Japanese Patent Laid-Open No. 247,884/9 and in Japanese Patent Laid-Open No. 97,725/93, the amount of CFCs generated is high in both of them: the amount of CFCs generated at a reaction temperature 350° C. is 1.7% in the former method and 2–3% at a reaction temperature of 360° C. in the latter method.

Further, the method is disclosed in Japanese Patent Laid-Open No. 146,832/89 as a fluorination reaction of tetrachloroethylene using a chromium catalyst. The catalyst is $Cr_2O_3$, prepared by pyrolysis of ammonium dichromate. The amount of CFCs generated, however, is not referred to at all.

In Japanese Patent Laid-Open No. 268,933/96, a fluorination method of tetrachloroethylene is disclosed that uses a mixed catalyst of MgO and $Cr_2O_3$. Tests were performed with several mixed catalysts having different ratios of the amount of MgO to $Cr_2O_3$. When using a catalyst having a Cr content which minimizes the ratio of CFCs/HFC-125, the conversion rate of tetrachloroethylene is about 93% at a reaction temperature of 320° C. and the ratio of CFCs/HFC-125 is 2.9%. The amount of CFCs generated itself is lower if the ratio of MgO is higher, whereas the conversion rate of tetrachloroethylene is lower; it is also shown that increasing the Cr content in order to obtain a higher conversion rate results in an increase in the amount of CFCs generated by two-fold at a maximum.

OBJECT OF THE INVENTION

The resent invention was carried out in consideration of the above situation. The object is to provide a manufacturing method for fluorine-containing ethane in which, when obtaining the fluorine-containing ethane having HFC-125 as the main reaction product through a fluorination reaction that uses tetrachloroethylene or HCFC-123 or HCFC-124 as the starting material, generation of CFC by-products can be controlled to be as low as possible by improving the catalyst used in the fluorination reaction.

CONSTITUTION OF THE INVENTION

The manufacturing method of the present invention for the fluorine-containing ethane that has HFC-125 as the main component by fluorination of at least one selected from the group composed of tetrachloroethylene, HCFC-123 and HCFC-124 with hydrogen fluoride, is characterized by using fluorochromium oxide that has not less than 30 wt. % of fluorine content as the catalyst.

By increasing the fluorine content of the fluorochromium oxide catalyst, fluorine-containing ethane having HFC-125 as the main component can be manufactured while controlling the generation of CFC by-products to be as low as possible when applying this catalyst to the fluorination reaction of the starting material described above. Herein, however, as the manufactured fluorine-containing ethane, HCFC-123 and/or HCFC-124 are usually included in addition to the HFC-125 as described later.

The starting material of the present invention is either a single material selected from tetrachloroethylene, HCFC-12 and HCFC-124 or a mixture of two or more of them.

The above HCFC-124 can be obtained by, for example, fluorination of HCFC-123 or reduction of CFC-114a (2,2-dichloro-1,1,1,2-tetrafluoroethane). The above described HCFC-123 can be obtained by, for example, fluorination of tetrachloroethylene, chlorination of HCFC-133 (2-chloro-1,1,1-trifluoroethane) or reduction of CFC-113a (1,1,1-trichloro-2,2,2-trifluoroethane). In addition, the above tetrachloroethylene is manufactured by an industrially common method, e.g. chlorination of hydrocarbon or its chlorine derivatives at its own pyrolysis temperature.

Now even when carrying out a fluorination reaction by HF using these selected starting materials, the ratio of CFCs/HFC-125 cannot be kept low by conventional methods. The mechanism of the generation of CFCs as by-products is described as follows.

If the starting material is HCFC-124, the conversion rate to HFC 125 cannot reach 100% under ordinary reaction conditions and unreactive HCFC-124 exists in the reactor. This unreactive HCFC-124 will generate HCFC-123 resulting from the reaction with a by-product, HCl.

On the other hand, if the starting material is HCFC-123, the organic substances at the exit of the reactor after the fluorination reaction are mainly fluorinated HCFC-124, HFC-125 tetrachloroethylene chlorinated by HCl, which is a by-product, and unreactive HCFC-123.

Similarly, if the starting material is tetrachloroethylene, the organic substances at the exit of the reactor are mainly HCFC-123, HCFC-124 and HFC-125.

From these gases which passed through the reactor, the gas with HFC-125 as the main component is separated and the remaining gas is recycled to the reactor to improve the yield. This, whatever the starting material may be, fluorination of the mixture mainly consisting of tetrachloroethylene, HCFC-123 and HCFC-124 will proceed in the reactor although the amount of each is different. Therefore, HCFC-133a and HFC-134a (1,1,1,2-tetrafluoroethane), which are by-products if tetrachloroethylene is the starting material, and CFCs such as CFC-113a, CFC-114a and CFC-115 are generated. CFCs generated in such reactions do not convert to HFC-125 by the fluorination reaction and will be lost in production. All of the C C-113a and CFC-114a are fluorinated to CFC-115 by recycling the reaction gases. Since the boiling point of CFC-115 is close to that of HFC-125 and the relative volatility is close to 1, separation is difficult in an ordinary fractionator. Removing these requires separate facilities for extractive distillation which will increase costs. Further, CFCs are banned substances as described above, because they destroy the ozone layer, and it is necessary to minimize their discharge in order to protect the global environment. For these reasons, the amounts of CFCs generated including CFC-115 should be reduced as far as possible.

The present inventors have examined earnestly a fluorinaton reaction of tetrachloroethylene, HCFC-123 and HCFC-124 to achieve the present invention and have found that the ratio of CFCs/HFC-125 (if tetrachloroethylene is the starting material, the ratio of CFCs to the total of HCFC-123, HCFC-124 and HFC-125) is not more than 0.5% when performing a fluorination reaction using a fluorochromium oxide catalyst in which the content of fluorine is not less than 30 wt. % at a reaction temperature of 300° C. when tetrachloroethylene is the starting material, is not more than 1.0% when HCFC-123 is the starting material, and is not more than 0.1% when HCFC-124 is the starting material, at a reaction temperature of 315° C.

For the chromium oxide necessary for preparation of the catalyst, one which is highly active with a specific surface area of not less than 120 m²/g is preferable as disclosed in Japanese Patent Laid-Open No. 146,680/93. In the present invention, the chromium oxide is further fluorinated to have a fluorine content of not less than 30 wt. % an submitted to the reaction. Therefore, for example, when charging the chromium oxide (unfluorinated substance) into the reactor, the chromium oxide can be fluorinated at least at the step immediately before the fluorination reaction of the above starting materials to give fluorochromium oxide.

Fluorination of the chromium oxide may be performed using any known method such as the one described in Japanese Patent Laid-Open No. 146,680/93. In order to increase the fluorine content, for example, the chromium oxide may be treated with HF at a high temperature for an extended time. Actually, when the chromium oxide was treated with HF at 360° C. for 2 hr, fluorochromium oxide with a fluorine content of 31.4 wt. % was obtained.

In the present invention, fluorochromium oxide prepared by a method other than the above as well as fluorochromium oxide already used as a catalyst in the fluorination reaction of halogenated hydrocarbon can be used as suitable catalysts. Namely, if fluorochromium oxide which has a lower fluorine content before the reaction is used over an extended time in the fluorination reaction of halogenated hydrocarbon, it will come to have a higher fluorine content of not less than 30 wt. % which is suitable for the present invention. Actually, in the experiment where the fluorination reaction of HCFC-133a was performed where the molar ratio of HF/HCFC-133a was 4 at a reaction temperature of 350° C. for 140 hr, fluorochromium oxide which has a fluorine content of 35.2 wt. % was obtained.

The present inventors have found that it is extremely significant not to simply fluorinate chromium oxide, but to fluorine it as prepared with a fluorine content of not less than 3 wt. %. According to the findings of the present inventors, when the fluorination rate (the fluorine content) of chromium oxide has been adjusted to not less than 30 wt. %, the objective HFC-125 is obtained with high selectivity and generation of CFCs can be well controlled. The preferred range for the fluorine content is between 30 wt. % and 45 wt. %.

In the resent invention, although no specific limits are set on the specific surface area of the fluorochromium oxide catalyst, the range is usually 25 m²/g–130 m²/g, and preferably 40 m²/g–100 m²/g.

The fluorination reaction of the starting materials with HF in the present invention is usually conducted at a reaction temperature of 250–400° C., and preferably 280–350° C. If the contact temperature and the molar ratio are the same the conversion rate to HFC-125 increases as the reaction temperature becomes higher. However, it is necessary to select the reaction temperature carefully since it has a large effect on the amount of by-products generated.

Also the ratio of HF used in the fluorination reaction to the starting material as described above is not specifically limited in the present invention. However, the molar ratios of HF to tetrachloroethylene, HF to HCFC-124, and HF to HCFC-123, are usually selected from the range 1.5:1 to 15:1 and preferably 2:1 to 9:1. Specifically, it is preferable to conduct the fluorination reaction while increasing the ratio of the HF amount to reduce the amount of CFCs generated, which has the disadvantage of degrading the economics of the process itself because it increases the amount of HF recycled. Therefore, taking both conditions into consideration, well-balanced individual reaction conditions are more practical when conducting the fluorination reaction.

In the resent invention, there is no specific limit on the pressure of the fluorination reaction of the starting materials, however, since separation of the products and the purfication process are advantageous under certain pressure conditions, this may be decided based on these condition. The range of reaction pressures usually adopted is 0.01 MPaG–2.0 MPaG.

In the present invention, the gas containing HFC-125 which is the main component produced by the fluorination reaction the starting material is separated and recovered once. Thereafter it is desirable to recycle the residue containing HCFC-123 and/or HCFC-124 back into the reactor multiple times. This is associated with improving the yield of HFC-125 and one of the most significant results of this invention 5 that generation of CFCs can be also controlled by this recycling.

When performing the present invention, it is sometimes necessary to pay attention to the phenomenon of deterioration of the catalyst over time.

In the event that deterioration of the catalyst becomes particularly problematic in the present invention, it is preferable and effective to include oxygen of 0.1 mol. % to 16 mol. % in the starting material to effectively prevent the deterioration.

INDUSTRIAL APPLICATION

In the manufacturing method for fluorine-containing ethane of the present invention, fluorine-containing ethane containing HFC-125 as a main component can be manufactured with a large degree of control over the generation of CFCs because when fluorinating the starting materials selected, either singly or as a mixture, from the group composed of tetrachloroethylene, HCFC-123 and HCFC-124 with hydrogen fluoride, a highly specified fluorochromium oxide with a fluorine content of not less than 30 wt. % is used as the catalyst.

EXAMPLE

The following Examples will be given to further illustrated the present invention. However, it should be understood that the present invention is not limited to these Examples.

Example 1

The fluorochromium oxide catalyst was prepared as described below. First, 10% ammonia water was added to 765 g of 5.7% aqueous chromium nitrate. After the obtained precipitate was filtered and washed, this was dried in air at 120° C. for 12 hr to give chromium hydroxide. This chromium hydroxide was molded to pellets of 3.0 mm in diameter and 3.0 mm in height which were calcined at 400° C. for 2 hr in a flow of nitrogen gas to give chromium oxide.

Next, the chromium oxide was gradually heated to 200° C. –360° C., and when it reached 360° C., it was fluorinated with hydrogen fluoride for 220 hr to give fluorochromium oxide. The resulting specific surface area of this fluorochromium oxide by the BET method was 70 m$^2$/g and the fluorine content was 31.4 wt. %.

Subsequently, using this fluorochromium oxide as the catalyst, a fluorination reaction of HCFC-124 was performed under the following conditions: 10 g of the catalyst was used; the flow rate of the HCFC-124 was 50 Nml/min; the flow rate of the HF was 100 Nml/min; the W/Fo was 4 (g·sec·Nml$^{-1}$); the molar ratio of HF/HCFC-124 was 4; and the reaction temperature as 315° C. Then the catalyst was charged in a Hastelloy C reaction tube 15 mm in internal diameter for the reaction. After washing the reaction gas with water, it was analyzed by gas chromatography using a Polapack Q column. The results are given in Table 1.

TABLE 1

| W/Fo | HF/HCFC-124 Molar Ratio | Reaction Temperature (° C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 2 | 315 | 10.9 | 33.3 | 55.6 | 0.123 | 0.221 |

* W: Catalyst weight (g), Fo: Gas flow rate converted to standard state (ml/sec).

Example 2

Except that fluorochromium oxide (fluorine content: 35.2 wt. %) used in the fluorination reaction of HCFC-133a was used, the fluorination reaction of HCFC-124 was performed under conditions similar to Example 1. The reaction results are given in Table 2.

TABLE 2

| W/Fo | HF/HCFC-124 Molar Ratio | Reaction Temperature (° C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 2 | 315 | 10.6 | 40.4 | 48.9 | 0.073 | 0.150 |

Example 3

Except that fluorochromium oxide (fluorine content: 41.5 wt. %) used in the fluorination reaction of HCFC-133a was used, the fluorination reaction of HCFC-124 was performed under conditions similar to Example 1. The reaction results are given in Table 3.

TABLE 3

| W/Fo | HF/HCFC-124 Molar Ratio | Reaction Temperature (° C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 2 | 315 | 10.4 | 47.4 | 42.1 | 0.042 | 0.099 |

Comparative Example 1

Except using a catalyst (specific surface area: 140 m$^2$/g, fluorine content: 12 wt. %; referred to as a "lower fluorinated catalyst") obtained under conditions for the fluorination of chromium oxide at 200° C. for 2 hr, the fluorination reaction of HCFC-124 was performed under conditions similar to Example 1. The reaction results are given in Table 4.

TABLE 4

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 2 | 315 | 11.1 | 26.0 | 62.6 | 0.176 | 0.281 |

Example 4

Except setting the flow rate of HCFC-124 to 100 Nml/min, the flow rate of HF to 200 Nml/min, and the W/Fo to 2(g·sec·Nml$^{-1}$), the fluorination reaction of HCFC-124 was perform under conditions similar to Example 2. The reaction results, are given in Table 5.

TABLE 5

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 2 | 2 | 315 | 6.7 | 56.6 | 36.6 | 0.037 | 0.100 |

Comparative Example 2

Except using a catalyst (fluorine content: 25 wt. %) obtained under conditions for the fluorination of chromium oxide at 360° C. for 155 hr, the fluorination reaction of HCFC-124 as performed under conditions similar to Example 1. The reaction results are given in Table 6.

TABLE 6

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 2 | 315 | 11.0 | 28.2 | 60.3 | 0.157 | 0.260 |

Comparative Example 3

Except using the lower fluorinated catalyst used in Comparative Example 1, the fluorination reaction of HCFC-124 was performed under conditions similar to Example 4. The reaction results are given in Table 7.

TABLE 7

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 2 | 2 | 315 | 8.2 | 44.6 | 47.1 | 0.081 | 0.172 |

Example 5

Except setting the molar ratio of HF/HCFC-124 to 4, the flow rate of HCFC-124 to 30 Nml/min, and the flow rate of HF to 120 Nml/min, the fluorination reaction of HCFC-124 was performed under conditions similar to Example 2. The reaction results are given in Table 8.

TABLE 8

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 4 | 315 | 6.5 | 40.7 | 52.7 | 0.044 | 0.084 |

Comparative Example 4

Except using a lower fluorinated catalyst used in Comparative Example 1, the fluorination reaction of HCFC-124 was performed under conditions similar to Example 5. The reaction results are given in Table 9.

TABLE 9

| W/Fo | HF/HCFC-124 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 4 | 315 | 6.6 | 31.0 | 62.2 | 0.079 | 0.128 |

Example 6

Except setting HCFC-123 as the starting material, the flow rate of HCFC-123 to 30 Nml/min, the flow rate of HF to 120 Nml/min, the W/Of to 4 (g·sec·Nml$^{-1}$), the molar ratio of HF/HCFC-123 to 4, and the reaction temperature to 315° C., the fluorination reaction was performed under conditions similar to Example 2. The reaction results are given in Table 10.

TABLE 10

| W/Fo | HF/HCFC-123 Molar Ratio | Reaction Temperature (°C.) | Concentration in Organic Substances (%) | | | | CFCs/HFC-125 (%) |
|---|---|---|---|---|---|---|---|
| | | | HCFC-123 | HCFC-124 | HFC-125 | CFCs | |
| 4 | 4 | 315 | 35.4 | 32.9 | 31.2 | 0.251 | 0.806 |

Comparative Example 5

Except using the lower fluorinated catalyst used in Comparative Example 1, the fluorination reaction of HCFC-123 was performed under conditions similar to Example 6. The reaction results are given in Table 11.

TABLE 11

| W/Fo | HF/HCFC-123 Molar Ratio | Reaction Temperature (°C) | Concentration in Organic Substances (%) HCFC-123 | HCFC-124 | HFC-125 | CFCs | CFCs/HFC-125 (%) |
|---|---|---|---|---|---|---|---|
| 4 | 4 | 315 | 29.1 | 29.9 | 40.4 | 0.432 | 1.07 |

Example 7

Using the same catalyst as in Example 2, the fluorination reaction was performed using tetrachloroethylene (represented as $C_2Cl_4$ in the Table) as the starting material. The reaction was performed under the following conditions: amount of tetrachloroethylene supplied was 0.22 g/min; the flow rate of HF was 270 Nml/min; the molar ratio of HF/tetrachloroethylene was 9; and the W/Fo was 2. The reaction results are given in Table 12. Herein, in the reaction of tetrachloroethylene, the ratios of CFCs to the total (hereinafter represented as 12X) of HCFC-123, HCFC-124 and HFC-125 are shown in the Table.

TABLE 12

| W/Fo | HF/$C_2Cl_4$ Molar Ratio | Reaction Temperature (°C) | Concentration in Organic Substances (%) HCFC-123 | HCFC-124 | HFC-125 | CFCs | 12X (%) |
|---|---|---|---|---|---|---|---|
| 2 | 9 | 300 | 22.3 | 13.6 | 4.01 | 0.169 | 0.423 |

Comparative Example 6

Except using the same catalyst as used in Comparative Example 1 in the reaction in Example 7, the fluorination reaction of tetrachloroethylene was performed under conditions similar to Example 7. The reaction results are given in Table 13.

TABLE 13

| W/Fo | HF/$C_2Cl_4$ Molar Ratio | Reaction Temperature (°C) | Concentration in Organic Substances (%) HCFC-123 | HCFC-124 | HFC-125 | CFCs | 12X (%) |
|---|---|---|---|---|---|---|---|
| 2 | 9 | 300 | 25.1 | 13.0 | 2.81 | 0.271 | 0.662 |

Example 8

Except supplying 1 mol % oxygen to tetrachloroethylene in the reaction gas, the fluorination reaction of tetrachloroethylene performed under conditions similar to Example 7. The reaction results are given in Table 14. Significant reduction in the catalyst activity due to deterioration was not observed even after reaction for 1,000 hr.

TABLE 14

| W/Fo | HF/$C_2Cl_4$ Molar Ratio | Reaction Temperature (°C) | Concentration in Organic Substances (%) HCFC-123 | HCFC-124 | HFC-125 | CFCs | 12X (%) |
|---|---|---|---|---|---|---|---|
| 2 | 9 | 300 | 15.4 | 6.80 | 1.22 | 0.311 | 1.33 |

Comparative Example 7

Except using the same catalyst as used in Comparative Example 1 in the reaction in Example 8 the fluorination reaction of tetrachloroethylene was performed under conditions similar to Example 8. The reaction results are given in Table 15.

TABLE 15

| W/Fo | HF/$C_2Cl_4$ Molar Ratio | Reaction Temperature (°C) | Concentration in Organic Substances (%) HCFC-123 | HCFC-124 | HFC-125 | CFCs | 12X (%) |
|---|---|---|---|---|---|---|---|
| 2 | 9 | 300 | 16.2 | 7.49 | 1.37 | 0.385 | 1.54 |

As shown in each Example, it is understood that if catalyst which fulfil the present inventive conditions are used for the fluorination reactions of the starting materials, the generation of CFCs can be fully controlled and the objective products can be obtained with good selectivity even when modifying the reaction conditions and the starting material. To the contrary, as shown in each Comparative Example, sing catalysts out of the present inventive condition will not have a significant effect on controlling the generation of CFCs.

What is claimed is:

1. A manufacturing method for fluorine-containing ethane characterized by that fluorochromium oxide with a fluorine content of not less than 30 wt. % is used as a catalyst when fluorine-containing ethane which contains 1,1,1,2,2-pentafluoroethane as the main component is obtained by fluorinating at least one selected from the group consisting of tetrachloroethylene, 2,2-dichloro-1,1,1-trifluoroethane and 2-chloro-1,1,1,2-tetrafluoroethane with hydrogen fluoride.

2. A manufacturing method for fluorine-containing ethane as claimed in claim 1 wherein the fluorine content of said fluorochromium oxide catalyst is 30–45 wt. %.

3. A manufacturing method for fluorine-containing ethane as claimed in claim 1 wherein fluorine-containing ethane also containing 2-chloro-1,1,1,2-tetrafluoroethane and/or 2,2-dichloro-1,1,1-trifluoroethane as reaction products is obtained.

4. A manufacturing method for fluorine-containing ethane as claim d in claim 1 wherein 2-chloro-1,1,1,2-tetrafluoroethane and/or 2,2-dichloro-1,1,1-trifluoroethane from the reaction mixture are mainly circulated in said fluorination reaction.

5. A manufacturing method for fluorine-containing ethane as claimed in claim 1 wherein said fluorochromium oxide catalyst is prepared by a fluorination reaction of chromium oxide.

6. A manufacturing method for fluorine-containing ethane as claimed in claim 1 wherein the fluorochromium oxide catalyst generated from the fluorination reaction of halogenated hydrocarbon is used as the said fluorochromium oxide catalyst.

* * * * *